United States Patent [19]

Agar et al.

[11] 4,362,048
[45] Dec. 7, 1982

[54] APPARATUS FOR USE IN THE MEASUREMENT OF A VARIABLE

[75] Inventors: Joram Agar, Grand Cayman, British West Indies; Gerald Anderson, New Alresford, England

[73] Assignee: Redland Automation Limited, England

[21] Appl. No.: 217,927

[22] Filed: Dec. 18, 1980

Related U.S. Application Data

[63] Continuation of Ser. No. 67,071, Aug. 15, 1979, abandoned.

[30] Foreign Application Priority Data

Jun. 4, 1979 [GB] United Kingdom ................ 7919367

[51] Int. Cl.³ .............................................. G01N 9/00
[52] U.S. Cl. ..................................... 73/32 A; 364/558
[58] Field of Search ................. 73/432 A, 1 R, 32 A; 364/550, 553, 556, 558, 571, 579, 581, 582

[56] References Cited

U.S. PATENT DOCUMENTS

| | | | |
|---|---|---|---|
| 3,763,692 | 10/1973 | Agar | 73/32 A |
| 3,790,910 | 2/1974 | McCormack | 364/558 |
| 4,060,715 | 11/1977 | Scott | 73/362 AR |
| 4,063,448 | 12/1977 | Agar | 73/32 A |

Primary Examiner—James J. Gill
Attorney, Agent, or Firm—Beveridge, DeGrandi & Kline

[57] ABSTRACT

Apparatus for use in the measurement of a variable comprises a housing; a first transducer which is mounted within the housing and which is arranged to produce an electrical transducer output signal which depends both on the value of the variable and on the value of at least one calibration constant of the transducer; an encoder which is mounted within said housing and which is programmed with information relating to the value of said at least one calibration constant, said encoder being arranged to produce an electrical encoder output signal representative of the value of the said at least one calibration constant, and connector means carried by said housing and electrically connected to the first transducer and to the encoder to receive signals functionally related to the transducer and encoder output signals, the connector means being connectible to a second transducer for the transmission of the said functionally related signals thereto.

18 Claims, 10 Drawing Figures

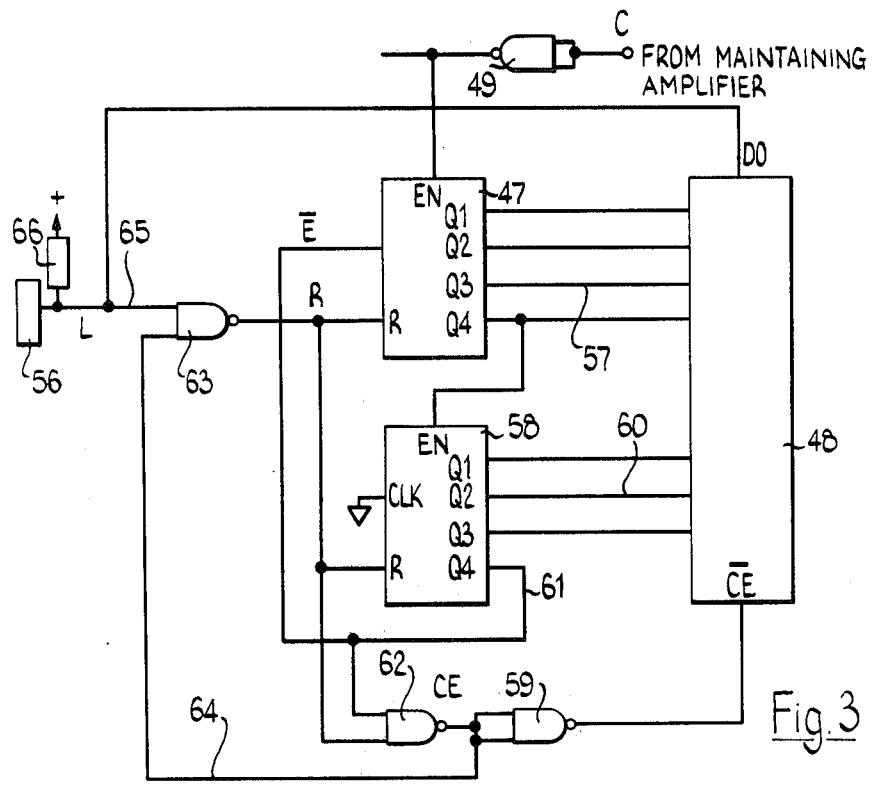
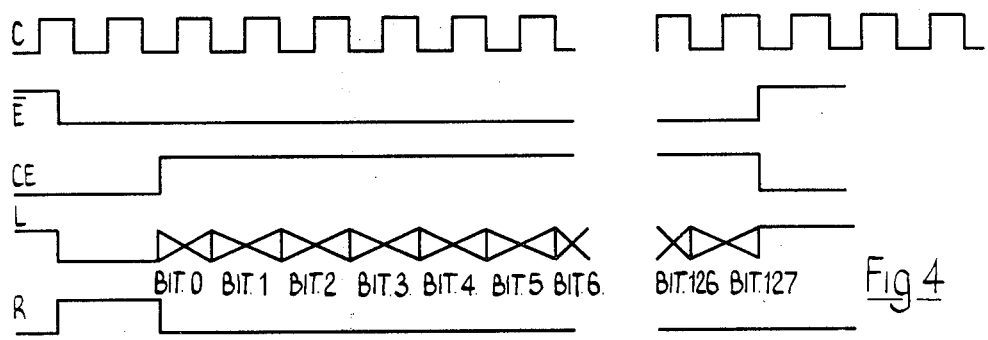
Fig.3
Fig.4

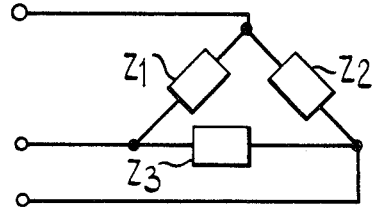
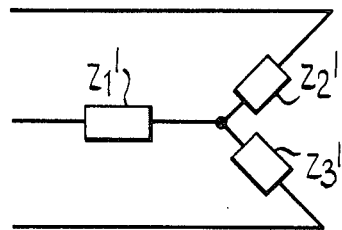
Fig. 5          Fig. 6
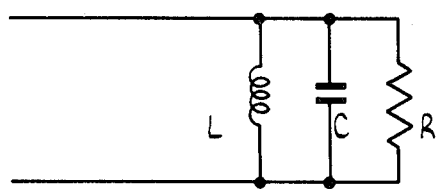
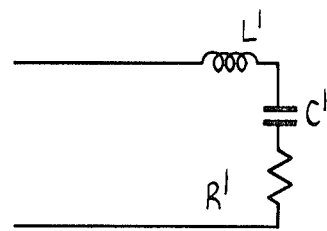
Fig. 7          Fig. 8
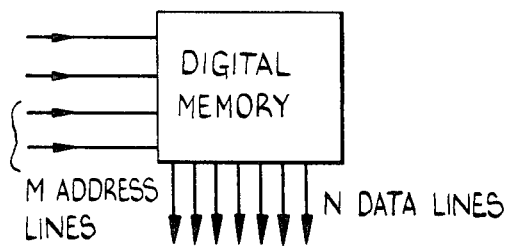
Fig. 9
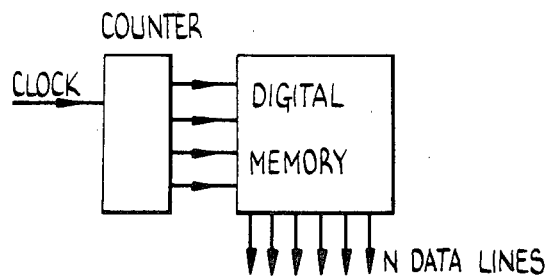
Fig. 10

APPARATUS FOR USE IN THE MEASUREMENT OF A VARIABLE

This is a continuation of application Ser. No. 067,071, filed Aug. 15, 1979, now abandoned.

FIELD OF THE INVENTION

This invention concerns apparatus for use in the measurement of a variable and, although the invention it is not so restricted, it is more particularly concerned with apparatus which comprises a frequency modulated transducer for producing an electrical signal whose frequency is representative of the density of a liquid or gas.

BACKGROUND OF THE INVENTION

A density meter, e.g. of the kind disclosed in British Pat. No. 1,175,586, is known which produces a frequency modulated electrical output signal of the form $$d = 2d_o \frac{(T - T_o)}{T_o} \left[ 1 + \frac{K}{2} \frac{(T - T_o)}{T_o} \right]$$

where
d = the density of the fluid
T = the period of the signal, and
$T_o$, K, and $d_o$ = calibration constants of the density meter.

In use, the said frequency modulated electrical output signal of the density meter is transmitted to a density converter. The latter converts the said output signal into an analog current which is linearly related to the density of the fluid passing through the density meter, the analog current being used to actuate a visual display indicative of the density. Alternatively, the density converter may produce a direct digital output or display of density.

In such an arrangement, the density converter has to be adjusted of, if computerised, has to have keyed in information as to the particular calibration constants of the density meter to which it is connected. This means that if a density meter breaks down in the field, not only is it necessary to replace the density meter, but it is also necessary to adjust the respective density converter or to key the necessary information into the latter, since no two density meters have exactly the same calibration constants.

If the density meter were to be used to measure the density of the fuel in an aircraft fuel tank, and if the density converter were to be constituted by a flight/fuel computer, then if the density meter were to break down, the flight/fuel computer would need to be adjusted and this could necessitate considerable testing of the latter before an aircraft provided therewith could be restored to an operational condition.

An object of the present invention is therefore to provide apparatus which may comprise such a density meter and which will be readily interchangeable with like apparatus without requiring the adjustment of the density converter or the keying of information into the latter.

Another object of the present invention is to provide apparatus suitable both in construction and in weight for use within, or extending through the wall of, an aircraft fuel tank for measuring the density of the fuel therein.

SUMMARY OF THE INVENTION

According to the present invention, there is provided apparatus for use in the measurement of a variable comprising a housing; a first transducer which is mounted within the housing and which is arranged to produce an electrical transducer output signal which depends both on the value of the variable and on the value of at least one calibration constant of the transducer; an encoder which is mounted within said housing and which is programmed with information relating to the value of said at least one calibration constant, said encoder being arranged to produce an electrical encoder output signal representative of the value of the said at least one calibration constant; and connecting means carried by said housing and electrically connected to the first transducer and to the encoder to receive signals functionally related to the transducer and encoder output signals, the connector means being connectible to a second transducer for the transmission of the said functionally related signals thereto. The said functionally related signals may be either identical to or different from the said transducer and encoder output signals.

Such apparatus may be used in combination with a second transducer arranged externally of said housing, said second transducer being electrically connected to the said connector means, the said second transducer being arranged to produce an indication of the value of the variable which is substantially unaffected by the value of said at least one calibration constant. As will be appreciated, in such a combination, the apparatus defined in the previous paragraph may be completely interchangeable with like apparatus having different calibration constants.

The encoder may comprise a counter arranged to receive clock pulses; and a memory which is programmed with the said information and which is addressed by the counter; the counter, on receiving the said clock pulses, sequentially addressing the memory to cause the latter to control the production of a pulse train output, which constitutes the encoder output signal, at the clock pulse frequency.

The transducer output signal may have a frequency which is representative of the value of the variable, the first transducer being connected to the encoder so that the latter receives therefrom clock pulses at the said frequency.

The transducer may comprise a vibratory member means for subjecting the vibratory member to a fluid whose density is to be measured; drive means for vibrating the vibratory member at a resonant frequency representative of said density; and detecting means, responsive to said resonant frequency, for producing the said transducer output signal.

The vibratory member is preferably a hollow vibratory member whose interior and exterior are subjected to the said fluid.

There may also be mounted within said housing a maintaining amplifier which is connected to the detecting means and which provides oscillatory power for driving the drive means. In this case, the counter may receive the said clock pulses from the maintaining amplifier, while the connector means may be connected to the first transducer by way of the maintaining amplifier.

Each of said drive means and detecting means may comprise a coil mounting member provided with a coil wound on a magnetic component, each coil mounting member being mounted in the housing and being formed of a material whose eddy current losses are substantially superior to those of the material of the housing, the density of the housing being substantially less than that of the coil mounting members.

The housing may be made of aluminium and the coil mounting members may be made of stainless steel.

The housing is preferably a tubular housing, the vibratory member being a tubular member which is mounted concentrically within the housing, the housing having angularly spaced apart radially extending apertures therethrough in which the said coil mounting members are mounted.

The housing preferably contains an unsealed compartment within which the first transducer is mounted, and a sealed compartment within which the encoder is mounted, the housing being provided externally with the said connector means which is sealed from but electrically connected to the encoder.

At least a portion of the said housing may be mounted in an aircraft fuel tank so that the first transducer is contacted by fuel in the aircraft fuel tank.

BRIEF DESCRIPTION OF THE DRAWINGS

The invention is illustrated, merely by way of example, in the accompanying drawings, in which:-

FIG. 3 is a circuit diagram of components forming part of the apparatus of FIGS. 1 and 2, FIG. 4 is a waveform diagram of signals produced by said components, and FIGS. 5-10 illustrate diagrammatically alternative circuits which may be used in substitution to that shown in FIG. 3.

Terms such as "upper" and "lower", as used in the description below, are to be understood to refer to directions as seen in the accompanying drawings.

DESCRIPTION OF THE PREFERRED EMBODIMENTS

Figure 1:
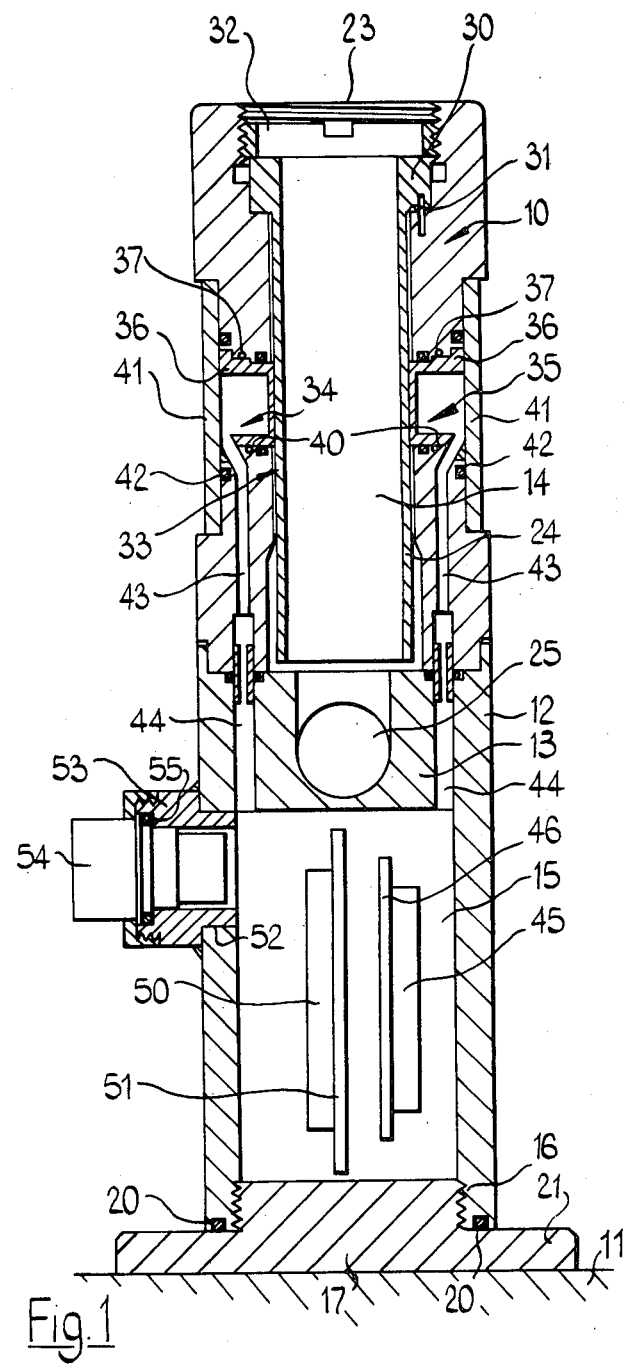
FIG. 1 is a cross-sectional view of apparatus according to the present invention for use in the measurement of density.
Figure 2:
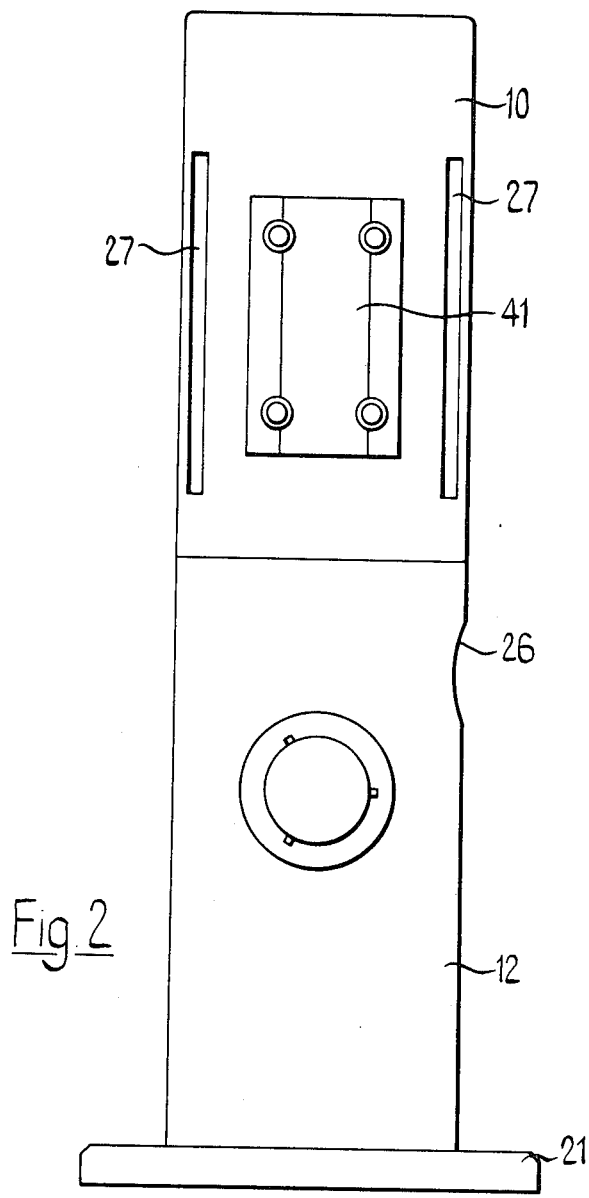
FIG. 2 is an elevation of the apparatus of FIG. 1.

In FIGS. 1 and 2 there is shown an apparatus 10 for use in the measurement of the density of the fuel in an aircraft fuel tank 11. The apparatus 10 comprises a housing 12, e.g. of aluminium, having a dividing wall 13 which divides the housing 12 into an upper unsealed compartment 14 and a lower sealed compartment 15. The sealed compartment 15 is sealed at its lower end 16 by an aluminium end cap 17 and "O" ring seals 20. The unsealed compartment 14, which is open at its upper end 23, also communicates with a passage 25 which passes through the dividing wall 13 and so extends to the exterior of the housing 12 at 26 (FIG. 2). The end cap 17 has an integral flange 21 which extends outwardly of the housing 12, the flange 21 having holes (not shown) therethrough for the passage therethrough of bolts (not shown) by means of which the flange 21 is bolted within the aircraft fuel tank 11 so that, in use, the whole of a vibratory sensing tube 24, which is mounted in the unsealed compartment 14, is completely submerged in the fuel therein. Alternatively, the flanges 21 may be bolted to the outside of the aircraft fuel tank in such a way that the housing 12 extends through the wall of the tank and into the interior of the latter.

The vibratory sensing tube 24 is preferably made of a magnetic stainless steel, the sensing tube 24 being mounted concentrically within the tubular member 12. The hollow interior of the sensing tube 24 is open to the fuel in the fuel tank. Thus the upper end of the sensing tube 24 communicates with the open upper end 23 of the housing 12, while the lower end of the sensing tube 24 communicates with the passage 25. Moreover, the region on the outside of the sensing tube 24 communicates with angularly spaced apart longitudinally extending slots 27 in the housing 12. Thus when the aircraft is in motion, the fuel will move about in the fuel tank 11, and will thus pass through and around the sensing tube 24. The housing 12 thus provides a "skeleton" housing about the sensing tube 24.

The sensing tube 24 has a flange 30 at its upper end which is held seated against an internal shoulder 31 of the housing 12 by means of a lock ring 32.

The sensing tube 24 forms part of a first or density transducer 33 for producing a frequency modulated electrical transducer output signal whose frequency depends both on the value of the density of the fuel within the sensing tube 24 and also on the value of the calibration constants $T_o$, K, and $d_o$ mentioned above. The density transducer 33 also comprises drive means 34 for vibrating the sensing tube 24 at a resonant frequency representative of the density of the fuel within the sensing tube, and detecting means 35, responsive to said resonant frequency, for producing the said transducer output signal.

Each of the drive means 34 and detecting means 35 comprises a coil mounting member 36 provided with a coil 37 wound on a magnetic component. The housing 12 has diametrically oppositely disposed radially extending apertures 40 therethrough in which the coil mounting members 36 are mounted. The coil mounting members 36 are made of stainless steel and thus of a material whose eddy current losses are substantially superior to those of the housing 12. That is to say, in order to reduce weight as much as possible, the housing 12 is made of aluminium and thus has a density substantially less than that of the coil mounting members 36. Aluminium, however, is a good conductor of electricity and therefore is unsuitable for use in the coil mounting members 36. The latter are therefore made of stainless steel to ensure low eddy current losses. The radially outer end of each of the coil mounting members 36 is closed by a cover plate 41 which is sealed by "O" ring seals 42 to the housing 12, the cover plate 41 being preferably made of a magnetic steel to provide some magnetic screening.

The housing 12 and the dividing wall 13 have aligned longitudinally extending passages 43, 44 respectively. Passing through the passage 43, 44 are leads (not shown) which extend between the drive means 34, detecting means 35 and a maintaining amplifier 50 which is mounted on a board 51 within the sealed compartment 15. The maintaining amplifier 50 provides oscillatory power for driving the drive means 34. Also mounted within the sealed compartment 15 is an encoder 45 mounted on a board 46. As explained more fully below, the encoder 45 includes counting means 47, 58 for counting clock pulses C (FIG. 3) from the maintaining amplifier 50 to which it is connected through an inverter 49 shown as constituted by a NAND gate with its inputs connected together. Since the maintaining amplifier 50 is itself connected to the detecting means 35, the frequency of the clock pulses C corresponds to the frequency of the said transducer output signal. Alternatively, the required clock pulses C could be produced by some further device (not shown).

The counting means is shown as consisting of two sections 47 and 58 and serves to address a digital memory 48. The counting section 47 connected to the maintaining amplifier 50 receives therefrom clock pulses C. The memory 48 (FIG. 3) may be programmed with the actual values of the said calibration constants or it may be programmed with the deviations of these actual values from nominal values. The counting means 47, 58 have reset terminals R. As will be seen, the counting means 47, 58 address the memory 48 sequentially up to a predetermined count, so that the encoder 45 controls the production of a pulse train output L (FIG. 4), containing discrete information in the form of a train of bits relating to the value of the said calibration constants. This pulse train output L constitutes the encoder output signal.

Mounted in an aperture 52 in the housing 12 is an externally extending housing 53 in which is mounted and from which is sealed by an O ring seal 55 an externally disposed 10-pin connector 54 which is electrically connected to the encoder 45 and to the amplifier 50. The connector 54 is, in use, connected to a second transducer 56 (FIG. 3) which is arranged externally of the apparatus shown in FIGS. 1 and 2 and which may be constituted by an aircraft flight/fuel computer. The second transducer 56, which is electrically connected to receive the bit output L from the encoder 45 and the output from the maintaining amplifier 50, is responsive to said outputs to produce (e.g. by means of a pointer moving over a scale or by a digital display) an indication of the value of the density, which indication is substantially unaffected by the value of the said calibration constants.

Consequently, if in use the apparatus shown in FIGS. 1–3 breaks down, it can be replaced by a similar apparatus which can be immediately connected to the second transducer 56, without any need to adjust or key information into the latter, because the second transducer 56 will "know" from the said pulse train output L what is the value of the calibration constants of the said similar apparatus. Thus the apparatus of FIGS. 1–3 is fully interchangeable with similar apparatus, notwithstanding the variation from one apparatus to the next of the said calibration constants.

In the circuit shown in FIG. 3, the clock pulse signal C (FIG. 3) from the maintaining amplifier 50 is transmitted to the counter section 47 and thence in cascade to the section 58. These sections are connected by address lines 57 and 60 to the digital memory 48 which has an output signal DO and an input signal $\overline{CE}$. The final Q4 output line 61 from the section 58 carries the signal $\overline{E}$ (FIG. 4) which is applied to one input of a NAND gate 62 at the output of which appears the signal CE (FIG. 4) which is applied via a further NAND gate 59, operating as an inverter, to the input of the memory 48 which accordingly receives the inverted signal $\overline{CE}$. The signal E is also fed back as shown to the counter section 47.

The bit signal output from the memory output terminal DO is fed at a line 65, which is connected to the positive terminal of a potential source through a suitable resistance 66, to the second transducer 56. This bit signal is also applied over the line 65 to one input of a NAND gate 63 the other input of which receives, over a line 64, the CE signal from NAND gate 62. The output of NAND gate 63 supplies a re-set signal R to the counter sections 47 and 58 and also to the remaining input of the gate 62.

The circuit shown in FIG. 3 operates as follows:

In the quiescent state, the signal $\overline{E}$ is HIGH and inhibits the counting means from counting up further. The output of the memory 48 is held in the high impedance state because the signal $\overline{CE}$ is held LOW. The line 65 is pulled to the HIGH state via the resistance 66. The circuit is triggered when the signal on the line 65 is made LOW by the second transducer 56. The output of the gate 63 accordingly becomes HIGH, the sections 47 and 48 are reset, and immediately release of $\overline{E}$ occurs. When the line 65 is released, it rises to HIGH briefly, allowing the signal $\overline{CE}$ to rise. The output of the memory 48 is put into the active state, and the first bit of data is fed to the line 65 from the memory output terminal DO and also to the second transducer 56. The counter sections count up at the clock rate (not necessarily from the maintaining amplifier 50) and each data bit is serially presented to the line 65. The data train may carry parity or Hamming codes in addition. Once the count reaches 128, $\overline{E}$ becomes HIGH and the circuit returns to the quiescent state. The memory 48 may be as known per se, and the counting means may be of the customary binary type comprising a sequence of cascaded flip-flops.

Since the sensing tube 24 is directly immersed in the fuel in the tank 11, a very accurate reading of density, as affected by pressure and temperature, can be obtained. At the same time, the sensing tube 24 is readily accessible for maintainance purposes.

Furthermore, the location of the encoder 45 and maintaining amplifier 50 in the tank 11 will significantly reduce the need for electro-magnetic screening and will reduce the wide range ambient temperature variations to which they would normally be subject, thereby leading to a significant increase in MTBF (mean time between failures).

In FIGS. 5–10 there are shown diagrammatically embodiments of encoders which may be used in substitution for that shown in FIG. 3. Thus FIG. 5 illustrates a three line passive decoder comprising impedances Z1, Z2, Z3 in delta connection and FIG. 6 illustrates a three line passive decoder with impedances Z1', Z2', Z3' in star connection. If either of these encoders is to be used in substitution for the encoder shown in FIG. 3 the three lines shown on the left hand side of the appropriate FIG. 5 or 6 would be passed through the connector 54 to the second transducer 56 which would include suitable circuitry, such as a bridge for example, for determining the values of Z1, Z2, or Z3 or Z1', Z2' or Z3' representative of the values of deviation from nominal of the constants.

FIG. 7 illustrates a two line passive analog encoder having circuit inductive, capacitative and resistive components, L, C, R in parallel connection and whose values may be determined at two frequencies and FIG. 8 illustrates a corresponding series connected arrangement having circuit components L', C', R'. If either of these encoders is to be used in substitution for that of FIG. 3 the two leads shown to the left of FIG. 7 or 8 would be connected to the second transducer 56 which would contain an AC bridge or an AC/DC bridge operable at at least two known frequencies and enabling said second transducer to evaluate the individual values of L, C and R, or L', C' R' representative of the values of deviation from nominal of the constants.

In the encoder shown in FIG. 9 there is a digital memory with address lines M, and parallel data lines N. If this encoder is to be used in substitution for that of FIG. 3, these lines (N and M) would be connected to the second transducer 56 through the connector 54 and the memory would contain non-volatile data representative of the values of the constants or deviations from nominal values. The second transducer would control the memory by sending addresses, either sequential or random, along the lines M and would receive the data thus requested along the lines N. If desired some or all of the data lines N could be multiplexed with the address lines M but, if this is done, the first transducer 33 would have to be provided with latches for effecting memory address storage and there would have to be some additional control logic.

FIG. 10 shows another form of encoder which could be substituted for that of FIG. 3. This comprises a digital memory with data lines N connected to a clocked counter as shown. If this encoder is to be used in place of that of FIG. 3, the data lines N would be passed through the connector 54 to the second transducer 56. The clock input line to the counter may also be passed through the connector to the second transducer or the said clock input could be taken from a clock provided in the first transducer 33. The information would be presented to the data lines N sequentially as the counter is clocked and the data read by the second transducer.

In the case of each of the encoders illustrated in FIGS. 5-10, the encoder may be interrogated by the second transducer 56 along one or more lines (not shown) to establish the analog or digital values of the pulse train output from the encoder, such analog or digital values representing either the value, or the deviation from a nominal value, of the calibration constant or constants.

I claim:

1. Apparatus for measurement of a fluid variable within a vessel comprising a housing adapted to be mounted in the vessel and including a sealed compartment and an unsealed compartment, said unsealed compartment being open for exposure to fluid in the vessel; a first transducer mounted within said unsealed compartment for exposure to fluid in the vessel for producing a transducer output signal dependent on both the value of the fluid variable and the value of at least one calibration constant of said transducer; a counter mounted within said sealed compartment and adapted to receive clock pulses; a memory mounted within said sealed compartment and programmed with information relating to the value of the at least one calibration constant, said counter responsive to an activating signal for addressing said memory to produce as an encoder output signal a pulse train at the frequency of clock pulses received by said counter, the pulse train containing information related to the at least one calibration constant; and connector means mounted externally on said housing, connected to said first transducer, said counter, and said memory, and adapted for connection to an output transducer, said connector means receiving the transducer output signal and the encoder output signal and, when connected to an output transducer, passing to the output transducer the transducer output signal and the encoder output signal and receiving from the output transducer an activating signal for application to said counter.

2. Apparatus as claimed in claim 1 in which the transducer output signal has a frequency which is representative of the value of the variable, the first transducer being connected to the counter so that the latter receives therefrom clock pulses at the said frequency.

3. Apparatus for measurement of the density of a fluid within a vessel comprising a housing adapted to be mounted in the vessel and including a sealed compartment and an unsealed compartment, said unsealed compartment being open for exposure to fluid in the vessel; a vibratory member mounted within said unsealed compartment for exposure to fluid in the vessel; a first coil mounting member including a first magnetic component; a drive coil wound on said first magnetic component; drive means for applying a drive signal to said drive coil to vibrate said vibratory member at a resonant frequency representative of the density of the fluid; a second coil mounting member including a second magnetic component; a detecting coil wound on said second magnetic component and responsive to the resonant frequency, for producing a transducer output signal dependent on both the density of the fluid and the value of at least one calibration constant of said vibratory member; each coil mounting member being mounted in said housing adjacent said vibratory member and being formed of a material whose eddy current losses are substantially superior to those of the material of said housing, the density of said housing being substantially less than that of said coil mounting members; an encoder mounted within said sealed compartment, said encoder programmed with information relating to the value of the at least one calibration constant; and connector means mounted externally on said housing, connected to said detecting coil and said encoder, and adapted for connection to an output transducer, said connector means receiving the transducer output signal and the encoder output signal and, when connected to an output transducer, passing to the output transducer the transducer output signal and the encoder output signal and receiving from the output transducer an activating signal for application to said encoder.

4. Apparatus for measurement of a fluid variable within a vessel comprising a housing adapted to be mounted in the vessel and including a sealed compartment and an unsealed compartment, said unsealed compartment being open for exposure to fluid in the vessel; a first transducer mounted within said unsealed compartment for exposure to fluid in the vessel for producing a transducer output signal dependent on both the value of the fluid variable and the value of at least one calibration constant of the transducer; an encoder mounted within said sealed compartment, said encoder having a high output impedance in its inactive state, programmed with information relating to the value of the at least one calibration constant, and responsive to an activating signal for producing an encoder output signal related to the at least one calibration constant; and connector means mounted externally on said housing, connected to said first transducer and said encoder, and adapted for connection to an output transducer, said connector means receiving the transducer output signal and the encoder output signal and, when connected to an output transducer, passing to the output transducer the transducer output signal and the encoder output signal and receiving from the output transducer, on the same line as that on which the encoder output signal passes, an activating signal for application to said encoder, whereby the same line is utilized both for receipt by said housing of the activation signal from the output transducer and application by the housing of the encoder output signal to the output transducer.

5. Apparatus as claimed in any one of claims 2, 1, or 4 in which the transducer comprises a vibratory member, means for subjecting the vibratory member to a fluid whose density is to be measured; drive means for vibrating the vibratory member at a resonant frequency representative of said density; and detecting means, responsive to said resonant frequency, for producing the said transducer output signal.

6. Apparatus as claimed in claim 5 in which the vibratory member is a hollow vibratory member whose interior and exterior are subjected to the said fluid.

7. Apparatus as claimed in claim 5 in which there is also mounted within said housing a maintaining amplifier which is connected to the detecting means and which provides oscillatory power for driving the drive means.

8. Apparatus as claimed in claim 7 in which the counter receives the said clock pulses from the maintaining amplifier.

9. Apparatus as claimed in claim 7 in which the connector means is connected to the first transducer by way of the maintaining amplifier.

10. Apparatus as claimed in claim 7 in which the maintaining amplifier is mounted in said sealed compartment.

11. Apparatus as claimed in claim 5 in which each of said drive means and detecting means comprises a coil mounting member provided with a coil wound on a magnetic component, each coil mounting member being mounted in the housing and being formed of a material whose eddy current losses are substantially superior to those of the material of the housing, the density of the housing being substantially less than that of the coil mounting.

12. Apparatus as claimed in claim 11 in which the housing is made of aluminium and the coil mounting members are made of stainless steel.

13. Apparatus as claimed in claim 11 in which the housing is a tubular housing, the vibratory member being a tubular member which is mounted concentrically within the housing, the housing having angularly spaced apart radially extending apertures therethrough in which the said coil mounting members are mounted.

14. Apparatus for measurement of the density of a fluid within a vessel comprising a housing adapted to be mounted in the vessel and including a sealed compartment and an unsealed compartment, said unsealed compartment being open for exposure to fluid in the vessel; a vibratory member mounted within said unsealed compartment for exposure to fluid in the vessel; drive means for vibrating the vibratory member at a resonant frequency representative of the density of the fluid; detecting means, responsive to the resonant frequency, for producing a transducer output signal dependent on both the density of the fluid and the value of at least one calibration constant of said vibratory member; an encoder mounted within said sealed compartment, said encoder programmed with information relating to the value of the at least one calibration constant and responsive to an activating signal for producing an encoder output signal related to the at least one calibration constant; connector means mounted externally on said housing and connected to said first transducer and said encoder; and a second transducer arranged externally of said housing, said second transducer being electrically connected to the said connector means to receive the transducer output signal and the encoder output signal, the first transducer passing to the second transducer the transducer output signal and the encoder output signal and receiving from the second transducer an activating signal for application to said encoder, the second transducer being arranged to produce an indication of the value of the variable which is substantially unaffected by the value of said at least one calibration constant.

15. Apparatus as claimed in any one on claims 1, 3, 4, or 14 in which at least a portion of said housing is mounted in an aircraft fuel tank so that the first transducer is contacted by fuel in the aircraft fuel tank.

16. Apparatus for measurement of the density of a fluid comprising an aircraft fuel tank for holding a fluid fuel; a housing at least a part of which is mounted in the fuel tank, and including a sealed compartment and an unsealed compartment, said unsealed compartment being open for exposure to fuel in the fuel tank; a vibratory member mounted within said unsealed compartment for exposure to fuel in the fuel tank; drive means for vibrating the vibratory member at a resonant frequency representative of the density of the fuel; detecting means, responsive to the resonant frequency, for producing a transducer output signal dependent on both the density of the fuel and the value of at least one calibration constant of said vibratory member; an encoder mounted within said sealed compartment, said encoder programmed with information relating to the value of the at least one calibration constant and responsive to an activating signal for producing an encoder output signal related to the at least one calibration constant; and connector means mounted externally on said housing, connected to said detecting means and said encoder, and adapted for connection to an output transducer, said connector means receiving the transducer output signal and the encoder output signal and, when connected to an output transducer, passing to the output transducer the transducer output signal and the encoder output signal and receiving from the output transducer an activating signal for application to said encoder.

17. In combination, apparatus as claimed in any one of claims 1, 3, 4, or 16 and a second transducer arranged externally of said housing, said second transducer being electrically connected to the said connector means and being arranged to produce an indication of the value of the variable which is substantially unaffected by the value of said at least one calibration constant.

18. Apparatus as claimed in claim 16 or 14 in which the encoder is a passive network.

* * * * *